US00PP35228P2

(12) United States Plant Patent
Bergman

(10) Patent No.: US PP35,228 P2
(45) Date of Patent: Jun. 20, 2023

(54) ***MANDEVILLA* PLANT NAMED 'MANZ0021'**

(50) Latin Name: *Madevilla sanderi*
Varietal Denomination: MANZ0021

(71) Applicant: SYNGENTA CROP PROTECTION AG, Basel (CH)

(72) Inventor: Wendy R. Bergman, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 17/803,548

(22) Filed: Aug. 18, 2022

(51) Int. Cl.
*A01H 5/02* (2018.01)
*A01H 6/08* (2018.01)

(52) U.S. Cl.
USPC ..... Plt./232

(58) Field of Classification Search
USPC ..... Plt./226, 232
See application file for complete search history.

*Primary Examiner* — Karen M Redden
(74) *Attorney, Agent, or Firm* — Dale Skalla

(57) ABSTRACT

A new *Mandevilla* plant named 'MANZ0021' particularly distinguished by its large light pink flowers, glossy and smooth dark green foliage, compact and bushy plant habit with excellent branching and flower production and fast flowering response.

1 Drawing Sheet

Latin name of the genus and species of the plant claimed: *Mandevilla sanderi* (Hemsl.) Woodson.

Varietal denomination: 'MANZ0021'.

BACKGROUND OF THE NEW PLANT

The present invention comprises a new *Mandevilla*, botanically known as *Mandevilla sanderi*, and hereinafter referred to by the variety name 'MANZ0021'.

'MANZ0021' is a product of a planned breeding program. The new cultivar has large light pink flowers, glossy and smooth dark green foliage, compact and bushy plant habit with excellent branching and flower production and fast flowering response.

'MANZ0021' originates from a hybridization made in a controlled breeding program in Amatitlan, Guatemala. The pollinations were made in 2012.

The female parent was an unpatented, proprietary plant identified as 'DIP-180' and differs from 'MANZ0021' by having white flowers, a more vigorous and more upright growth habit lighter green foliage and two weeks slower flowering response.

The male parent of 'MANZ0021' was an unpatented, proprietary plant identified as 'DIP-076' and differs from 'MANZ0021' by having a more compact growth habit, less freely branching, 20% larger foliage and two to three week slower flowering response.

The resulting seeds were sown in February 2014 and 'MANZ0021' was selected as one flowering plant within the progeny of the stated cross in December 2014 in a greenhouse in Gilroy, Calif.

The first act of asexual reproduction of 'MANZ0021' was accomplished when vegetative stem cuttings were propagated from the initial selection in February 2015 in a controlled environment in Gilroy, Calif.

BRIEF SUMMARY OF INVENTION

Horticultural examination of plants grown from cuttings of the plant initiated in June 2015 in Gilroy, Calif., and continuing thereafter, has demonstrated that the combination of characteristics as herein disclosed for 'MANZ0021' are firmly fixed and are retained through successive generations of asexual reproduction.

'MANZ0021' has not been observed under all possible environmental conditions. The phenotype may vary significantly with variations in environment such as temperature, light intensity and day length.

A Plant Breeder's Right for this cultivar has not yet been applied for. 'MANZ0021' has not been made publicly available prior to the effective filing date of this application, notwithstanding any disclosure that may have been made less than one year prior to the effective filing date of this application by the inventor or another who obtained 'MANZ0021' directly from the inventor.

The following traits have been repeatedly observed and are determined to be basic characteristics of the new variety. The combination of these characteristics distinguishes this *Mandevilla* as a new and distinct variety.

BRIEF DESCRIPTION OF THE PHOTOGRAPHS

Figure 1:
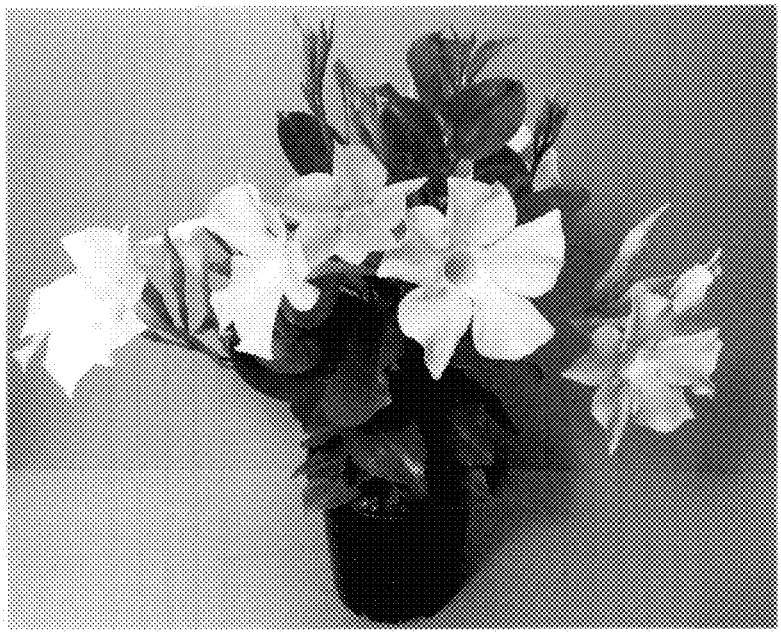
Figure 2:
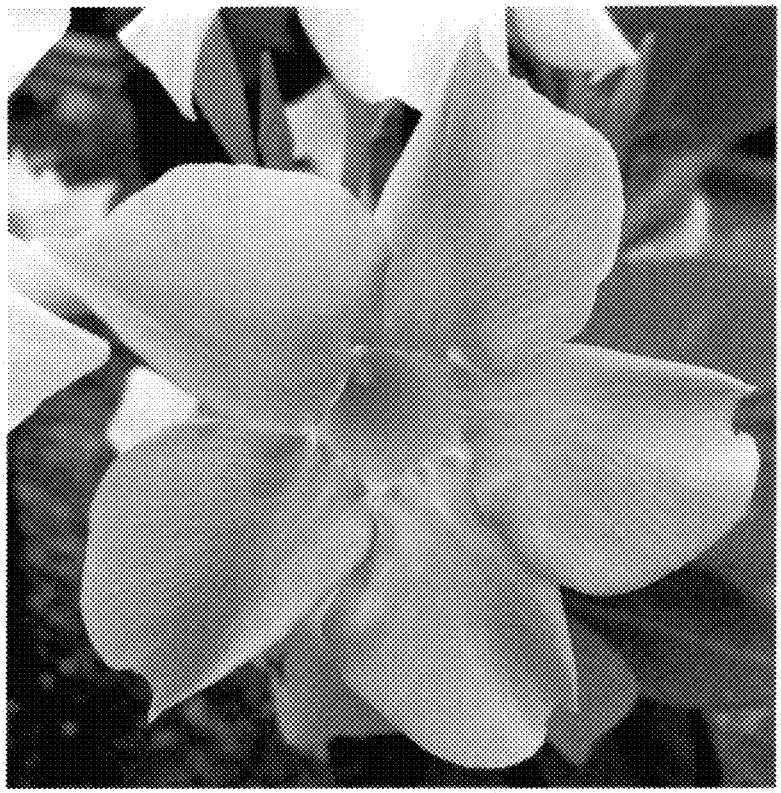

The accompanying photographic drawings show typical flower and foliage characteristics of 'MANZ0021' with colors being as true as possible with an illustration of this type. The photographic drawings show in FIG. 1, a flowering potted plant, approximately 6 months in age, of the new variety taken in Andijk, Netherlands in April 2020 and in FIG. 2, a close-up of a flower taken in Andijk, Netherlands in April 2018.

DETAILED BOTANICAL DESCRIPTION

The detailed botanical description was completed in July 2022 in Gilroy, Calif. The plants were growing in quart size pots in a greenhouse; they were about 6 months in age.

TABLE 1

DIFFERENCES BETWEEN THE NEW VARIETY 'MANZ0021' AND A SIMILAR VARIETY

| | 'MANZ0021' | 'FISRIX PINKA', U.S. Plant Pat. No. 20,644 |
|---|---|---|
| Flower production: | Produces 50-100% more flowers per plant | Produces 50-100% less flowers per plant |
| Flower color: | Lighter pink | Darker pink |
| Flowering response: | Two weeks faster | Two weeks slower |

Plant:

*Form, growth, and habit.*—Perennial or sub-shrub, herbaceous younger stems, woody at base of older stems, semi upright, with moderate tendency of developing vines depending on season and light intensity. Time for producing a commercial, flowering plant approximately is 20 weeks for one plant in a quart size container.

*Plant height.*—25 cm.

*Plant height (inflorescence included).*—29 cm.

*Plant width.*—29 cm.

Roots:

*Number of days to initiate roots.*—About 16-20 days at about 22 degrees C.

*Number of days to produce a rooted cutting plant.*—5 weeks at about 22 degrees C.

*Type.*—Fibrous, a little fleshy, free branching.

*Color.*—RHS 155D.

Foliage:

*Arrangement of leaves.*—Simple leaf, opposite and decussate.

*Immature leaf, color upper surface.*—RHS 137A.

*Immature leaf, color lower surface.*—RHS 138A.

*Mature leaf, color upper surface.*—RHS 139A.

*Mature leaf, color lower surface.*—RHS 137B.

*Length.*—6.3-8.5 cm.

*Width.*—3.8-5.1 cm.

*Shape.*—Ovate.

*Base shape.*—Rounded.

*Apex shape.*—Cuspidate.

*Margin.*—Entire.

*Texture, upper surface.*—Smooth, glossy, glabrous.

*Texture, lower surface.*—Smooth, glossy, glabrous.

*Pattern of leaf veins.*—Pinnate.

*Color of veins, upper surface.*—RHS 138B.

*Color of vein (midrib), lower surface.*—RHS 145C.

*Petiole color.*—RHS 137D.

*Length.*—1.1-1.3 cm.

*Diameter.*—0.2-0.25 cm.

*Petiole, texture.*—Glabrous.

Stem:

*Branching characteristics.*—Moderately free branching.

*Quantity of main branches per plant.*—4-5.

*Color of stem.*—RHS 143C.

*Length of stem.*—21-23 cm.

*Diameter (at about mid-point).*—0.3 cm.

*Length of internodes.*—1.5-4.2 cm.

*Stem, texture.*—Smooth and glabrous.

Inflorescence:

*Type of inflorescence.*—Raceme of several flowers, emerging from nodes of the stem.

*Number of flowers per inflorescence.*—5-7.

*Blooming habit.*—Continuously through the summer months.

*Quantity of flowers per plant.*—About 8 in various stages of development.

*Lastingness of individual blooms on the plant.*—Approximately 8-10 days, depending on temperature.

*Fragrance.*—Absent.

*Peduncle.*—

*Color.*—Green, RHS 143A.

*Length.*—2.0-4.4 cm.

*Diameter.*—0.25 cm.

*Texture.*—Smooth, glabrous, somewhat glossy.

Bud (just before opening/showing color):

*Color.*—Closest to RHS 65A with irregular tones of 62D.

*Length.*—6.6 cm.

*Width.*—1.6 cm.

*Shape.*—Elongated, spindle shape.

Immature flower:

*Diameter.*—5.8 cm.

*Vertical diameter.*—About 5.8 cm.

*Color upper surface.*—RHS 65A overlain with tones of 68B.

*Color lower surface.*—RHS 65A with irregular tones of 62D.

Mature flower:

*Shape.*—Funnelform, funnel shaped base, formed by 5 partly fused petals, with the petal lobes opening outwards, and a little overlapping.

*Flower, horizontal diameter.*—7.7 cm.

*Flower, vertical diameter.*—About 6.0 cm.

*Flower, diameter of the funnel.*—1.6 cm.

*Flower color, general.*—Light pink.

*Flower color, upper surface.*—RHS 65D with tones of RHS 65B.

*Flower color, lower surface.*—RHS 65D with slightly darker and lighter tones.

*Color of the funnel, inner side.*—Closest to RHS 14B.

*Color of the funnel, outside.*—RHS 65D with slightly darker and lighter tones.

*Petal, shape.*—Roughly ovate, asymmetric.

*Petal apex shape.*—Cuspidate.

*Petal base shape.*—Fused.

*Petal margin.*—Mainly entire and mildly undulate.

*Petal length, from the corolla opening.*—3.2 cm.

*Petal width, maximum.*—2.6 cm.

*Corolla, texture of upper surface.*—Glabrous, papillose.

*Corolla, texture of lower surface.*—Glabrous, papillose.

*Pedicel, color.*—Light green, RHS 144D.

*Length.*—1.8-2.2 cm.

*Diameter.*—0.25 cm.

*Pedicel, texture.*—Smooth, glabrous.

Calyx:

*Form.*—5 sepals, closely attached to the base of the flower.

*Color, visible outer surface.*—RHS 144D.

*Length.*—1.1 cm.

*Width.*—0.45 cm.

*Shape.*—Subulate.

*Apex shape.*—Acute.

*Based.*—Fused.

*Margins.*—Entire.

*Texture, upper surface.*—Glabrous.

Reproductive organs:

Gynoecium:

*Pistil.*—1, with a 5-lobed stigma.

*Style length.*—2.3 cm.

*Diameter.*—0.05 cm.

*Style color.*—RHS 145D.

*Stigma color.*—RHS 144C.

*Stigma shape.*—Five lobed.

*Ovary color.*—RHS 144D.

Androecium:

*Stamens.*—5, surrounding the style and stigma.

*Filaments.*—Fused with the base of the flower.

*Anther.*—Elongated.

*Anther color.*—RHS 159C.

*Anther length.*—0.9 cm.

*Color of pollen.*—RHS 4D.

*Pollen amount.*—Moderate.

Fertility/seed set: Has not been observed on this hybrid.

Disease/pest resistance: Has not been observed on this hybrid.

What is claimed is:

1. A new and distinct variety of *Mandevilla* plant named 'MANZ0021' substantially as illustrated and described herein.

* * * * *